United States Patent
Kramer et al.

(10) Patent No.: US 7,257,442 B2
(45) Date of Patent: Aug. 14, 2007

(54) MODE SWITCHING ALGORITHM FOR AV BLOCK

(75) Inventors: Andrew P. Kramer, Stillwater, MN (US); Gary T. Seim, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 168 days.

(21) Appl. No.: 10/854,736

(22) Filed: May 26, 2004

(65) Prior Publication Data

US 2005/0267538 A1    Dec. 1, 2005

(51) Int. Cl.
*A61N 1/00* (2006.01)
(52) U.S. Cl. ............................... 607/9; 607/4
(58) Field of Classification Search .............. 607/9, 607/4
See application file for complete search history.

(56) References Cited

U.S. PATENT DOCUMENTS

| | | | |
|---|---|---|---|
| 4,561,442 A * | 12/1985 | Vollmann et al. | 607/15 |
| 5,133,350 A | 7/1992 | Duffin | |
| 5,144,949 A * | 9/1992 | Olson | 607/17 |
| 5,318,594 A | 6/1994 | Limousin et al. | |
| 5,643,326 A | 7/1997 | Weiner et al. | |
| 6,397,105 B1 | 5/2002 | Bouhour et al. | |
| 2003/0078627 A1 * | 4/2003 | Casavant et al. | 607/9 |
| 2004/0260349 A1 * | 12/2004 | Stroebel | 607/9 |

* cited by examiner

*Primary Examiner*—Carl Layno
*Assistant Examiner*—Natasha Patel
(74) *Attorney, Agent, or Firm*—Schwegman, Lundberg, Woessner & Kluth, P.A.

(57) ABSTRACT

An apparatus and method is presented for treating patients with sinus node dysfunction who have apparently normal intrinsic AV conduction and thus do not require ventricular pacing unless there is an unexpected AV conduction failure. In one embodiment, a cardiac device with dual-chamber pacing capability is programmed to operate in a primary DDI (or DDI(R)) mode adjusted to pace only the atria if intrinsic AV conduction is intact and switch to a secondary DDD (or DDD(R)) mode upon detection of AV block.

20 Claims, 2 Drawing Sheets

MODE SWITCHING ALGORITHM FOR AV BLOCK

FIELD OF THE INVENTION

This invention pertains to cardiac rhythm management devices such as pacemakers and other implantable devices for treating cardiac dysfunction.

BACKGROUND

Cardiac rhythm management devices, which include pacemakers and implantable cardioverer/defibrillators (ICD), are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

Patients with sinus node dysfunction who are unable to maintain an adequate atrial rate (i.e., are chronotropically incompetent) but have intact intrinsic AV conduction are most appropriately treated with atrial pacing only such as AAI mode. (See the pacing modes section below for an explanation of the three-letter code for defining pacing modes.) Although ventricular pacing could also be delivered to these patients, it is preferable from a hemodynamic standpoint to utilize the native AV conduction system for stimulating the ventricles so that optimum atrio-ventricular synchrony is maintained. Also, several major clinical studies have demonstrated that unnecessary ventricular pacing is associated with a significantly increased risk of heart failure and atrial fibrillation in patients with dual-chamber pacemakers and ICDs.

Many patients with sinus node dysfunction, however, are at a higher risk than normal of developing another conduction system disorder such as some degree AV block. In AV block, the conduction of excitation from the atria to the ventricles is either slowed for blocked completely, resulting in atrioventricular dyssynchrony. Most physicians are therefore reluctant to program a pacemaker to AAI mode in patients with sinus node dysfunction because of the risk that they may at some time develop an AV block and need ventricular pacing. One way around this is to program the pacemaker with a dual-chamber mode which paces the atria and then the ventricles after a programmed AV delay interval (e.g., DDD mode) and specify a very long AV delay interval so that the ventricles are never paced as long as intrinsic AV conduction is intact. Such a mode, however, due to the length of the AV delay interval and its associated sensing refractory periods, may cause unacceptable loss of atrial and ventricular sensing capability which interferes with tachyarrhythmia detection. The programmed long AV delay interval also results in long nonphysiological AV delays causing atrioventricular dyssynchrony when ventricular pacing is required, which is clinically detrimental if it occurs for prolonged periods (referred to a pacemaker syndrome).

SUMMARY

The present invention relates to an apparatus and method for treating patients with sinus node dysfunction who have apparently normal intrinsic AV conduction and thus do not require ventricular pacing unless there is an unexpected AV conduction failure. In accordance with the invention, a cardiac device with dual-chamber pacing capability is programmed to operate in a primary DDI (or DDI(R)) mode adjusted to pace only the atria if intrinsic AV conduction is intact and switch to a secondary DDD (or DDD(R)) mode upon detection of AV block. The AV block mode switch feature gives the device the capability of treating sinus bradycardia without unnecessarily pacing the ventricles but with the safety of ventricular pacing if it becomes necessary. The primary DDI mode provides atrial pacing with ventricular backup pacing while not unduly interfering with tachyarrhythmia detection. The secondary DDD mode provides atrial and ventricular pacing in the presence of AV block and can be adjusted to maintain atrioventicular synchrony.

DETAILED DESCRIPTION

The basic approach of the present invention is to program a cardiac device with dual-chamber pacing capability such that it operates in a primary single-chamber atrial pacing mode while providing backup ventricular pacing in case the patient experiences a transient atrioventricular conduction failure, and it switches automatically to a secondary dual-chamber tracking mode if the patient experiences a sustained atrioventricular conduction failure. In an exemplary embodiment, the device is programmed to effectively operate in an AAI(R) primary mode by implementing the primary mode as DDI(R) with a long AV delay (e.g., 400 ms), which allows ventricular events to reset the atrial pacing timing and allows backup AV sequential ventricular pacing in case of first, second, or third degree AV block. The device switches to the DDD(R) secondary mode when the ventricle has been paced for more than a specified threshold number of beats, and then switches back to the DDI(R) mode after a period in DDD(R) to search for resumed intrinsic AV conduction. Another embodiment employs "hybrid timing" to limit rate oscillations due to backup ventricular pacing and mode switching, which is achieved by computing the ventriculoatrial pacing interval in DDI(R) mode with the intrinsic AV interval and/or the AV delay interval programmed for the DDD(R) mode. A more detailed explanation is set forth below preceded by a description of exemplary hardware components and basic pacing modes.

1. Exemplary Device Description

Conventional cardiac pacing with implanted pacemakers involves excitatory electrical stimulation of the heart by the delivery of pacing pulses to an electrode in electrical contact with the myocardium. The pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 1:
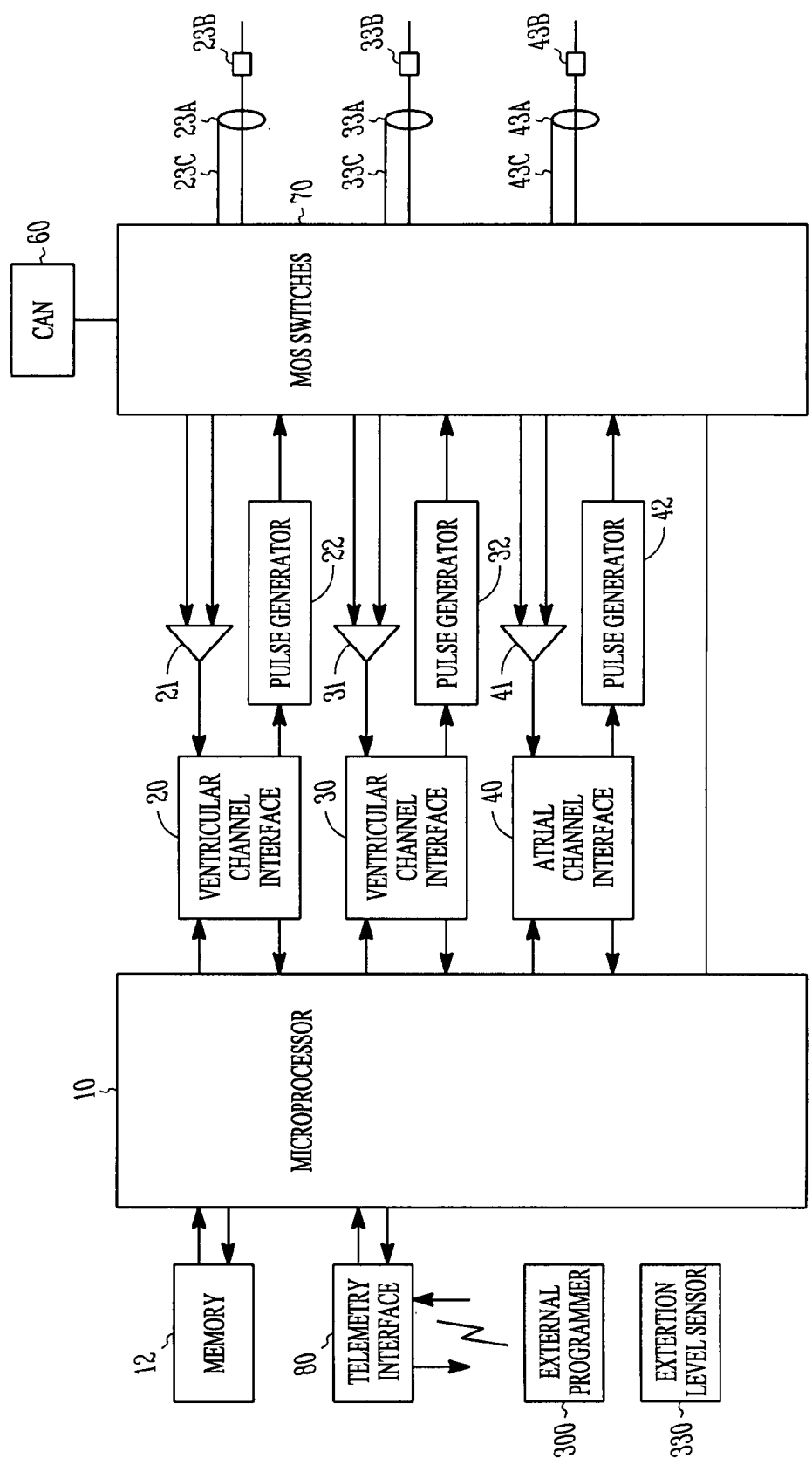
FIG. 1 is a block diagram of an exemplary cardiac device for practicing the present invention.

A system diagram of a pacemaker is shown in FIG. 1. (As the term is used herein, a "pacemaker" should be taken to mean any cardiac rhythm management device, such as an implantable cardioverter/defibrillator, with a pacing functionality.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with an associated display and input means that can interrogate the pacemaker and receive stored data as well as directly adjust the operating parameters of the pacemaker.

The embodiment shown in FIG. 1 has three available sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional single-chamber or dual-chamber pacing or biventricular pacing. In an example configuration, a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20. If the device is configured for biventricular pacing, a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. An electrogram is analogous to a surface electrocardiogram (ECG) and indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing. The exertion level sensor 330 (e.g., an accelerometer or minute ventilation sensor) provides an exertion level measurement which the controller uses to modulate the pacing rate in accordance with a rate-adaptive pacing algorithm.

2. Pacing Modes

The controller may be programmed to deliver pacing therapy in a number of different pacing modes. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval VEI for pacing the ventricles can be defined which is reset with each ventricular pace or sense. The interval between ventricular events is sometimes referred to as the cardiac cycle interval (CCI). An atrial escape interval can also be defined for pacing the atria either alone or in addition to pacing the ventricles. When only the atria are paced, the atrial escape interval is reset with each atrial pace or sense. In atrial tracking and AV sequential pacing modes, another ventricular escape interval is defined between atrial and ventricular events, referred to as the atrio-ventricular pacing delay (AVD) interval, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. In an AV sequential pacing mode, the atrio-ventricular delay interval is triggered by an atrial pace and stopped by a ventricular sense or pace. Atrial tracking and AV sequential pacing modes are commonly combined. When both the atria and ventricles are paced, the atrial escape interval starts with a ventricular sense or pace, is stopped by an atrial sense or pace, and is referred to as the ventriculoatrial (VA) interval. When both the atria and the ventricles are paced, the cardiac cycle interval CCI is equal to the sum of the VA interval and the AVD interval. Bradycardia pacing modes for dual-chamber pacemakers are commonly referred to by a three letter code where the first letter designates which chamber is paced (A or atrium, V for ventricle, D for both, and O for neither), the second letter designates which chamber is sensed, and the third letter designates what action is taken upon a sense (I for inhibiting a pace, T for triggering a pace, D for both triggering and inhibition, and O for no action). A fourth letter R is appended to the code if a rate-adaptive pacing mode is used.

3. AV Block Mode Switching

In accordance with the invention, an implantable cardiac device with dual-chamber pacing capability is programmed with a mode switching algorithm such that the device operates in a primary mode which provides atrial pacing to a patient and switches to a secondary mode which provides ventricular pacing upon failure of intrinsic AV conduction. In one embodiment, the device is operated in a primary DDI pacing mode adjusted to pace only the atria if intrinsic AV conduction is intact, and the device is switched to a secondary DDD pacing mode if N out of the last K cardiac cycles in the primary pacing mode were ventricular paced cycles, where N and K are specified integers. The primary and secondary pacing modes may also be rate-adaptive DDI(R) and DDD(R) modes, respectively.

The primary DDI mode may be implemented by programming the device to deliver an atrial pace upon expiration of a ventriculoatrial escape interval $VAI_{DDI}$ unless inhibited by an atrial sense, wherein the $VAI_{DDD}$ interval is triggered by a ventricular event and is derived as:

$$VAI_{DDI} = CCI - AV_S$$

when triggered by a ventricular sense and derived as:

$$VAI_{DDI} = CCI - AV_{DDD}$$

when triggered by a ventricular pace or, optionally, also when triggered by a PVC. The $AV_S$ value is a measured intrinsic AV delay interval, $AV_{DDD}$ is the value of a specified atrio-ventricular delay interval used in the secondary DDD mode, and CCI is a specified cardiac cycle interval representing a desired maximum interval between ventricular beats. The device is further programmed in the primary mode to deliver a ventricular pace upon expiration of a ventricular escape interval VEI unless inhibited by a ventricular sense, wherein the ventricular escape interval is reset by a ventricular pace or a ventricular sense and is set equal to:

$$VEI = CCI + (AV_{DDI} - AV_S)$$

where $AV_{DDI}$ is a desired maximum allowed interval after an atrial pace until a backup ventricular pace is to be delivered (e.g., 400 ms). The secondary DDD mode may be implemented by programming the device to deliver a ventricular pace upon expiration of an atrio-ventricular delay interval $AV_{DDD}$ unless inhibited by a ventricular sense, wherein the $AV_{DDD}$ interval is triggered by an atrial pace or sense and is set to a specified value. An atrial pace is delivered in the secondary mode upon expiration of a ventriculoatrial escape interval $VAI_{DDD}$ unless inhibited by an atrial sense, where the $VAI_{DDD}$ interval is triggered by a ventricular event and is derived as:

$$VAI_{DDD} = CCI - AV_S$$

when triggered by a ventricular sense and derived as:

$$VAI_{DDD} = CCI - AV_{DDD}$$

when triggered by a ventricular pace. In the DDI(R) and DDD(R) modes, the cardiac cycle interval CCI is modulated in accordance with a rate-adaptive pacing algorithm so that CCI varies from a base value equal to a specified lower rate limit LRL to a sensor-indicated rate computed by the rate-adaptive algorithm.

After switching to the secondary pacing mode, the device may be further programmed to operate in the secondary pacing mode for a specified number M of cardiac cycles and then return to the primary pacing mode. Alternatively, the device may be programmed to return to the primary pacing mode from the secondary pacing mode after evidence of intrinsic AV conduction is detected. Evidence of intrinsic AV conduction may be looked for by employing an AV search hysteresis algorithm in which the atrio-ventricular delay interval $AV_{DDD}$ is lengthened for one or more cycles while operating in the secondary pacing mode. Evidence of intrinsic AV conduction is detected if no ventricular paces are delivered with the lengthened $AV_{DDD}$ interval so that the device then returns to the primary pacing mode. In order to maintain an adequate pacing rate, the device may be programmed so that the atrio-ventricular delay interval $AV_{DDD}$ may be lengthened only if the cardiac cycle interval CCI as modulated by the rate-adaptive algorithm is not above the lower rate limit LRL by more than a specified limit value.

Figure 2:
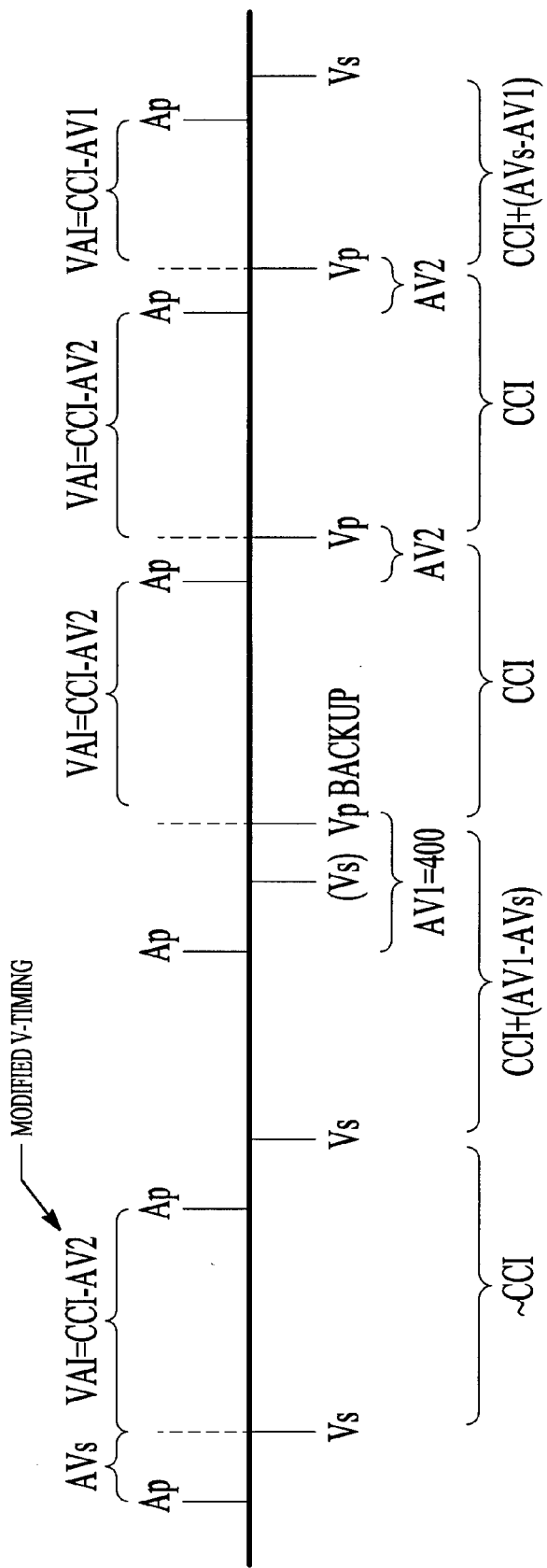
FIG. 2 is a timing diagram illustrating the operation of the AV block mode switch algorithm.

FIG. 2 is a timing diagram which illustrates an example of the AV block mode switching algorithm as described above. The device first operates in a primary DDI(R) mode where each atrial pace $A_P$ is followed by a ventricular sense $V_S$ due to intact intrinsic AV conduction. The interval between an atrial pace and the subsequent ventricular sense is measured as $AV_S$ and used to derive the ventriculoatrial interval for delivering the next atrial pace. When AV block occurs, no ventricular sense occurs at the expected time after an atrial pace, designated as $(V_S)$, and a backup ventricular pace is delivered at an interval after the atrial pace equal to the value of the $AV_{DDI}$ interval, designated as AV1 in the figure and an exemplary value for which is 400 ms. This is implemented by setting the ventricular escape interval initiated by a ventricular sense equal to $CCI + (AV1 - AV_S)$. In this example, the device switches to the secondary DDD(R) mode after one ventricular pace (alternatively, after N paced beats) so that the next atrial pace is delivered at a ventriculoatrial interval derived from the cardiac cycle interval CCI and the value of the $AV_{DDD}$ interval, designated as AV2 in the figure. After two paced beats in this example (alternatively, after M paced beats), the device lengthens the AV delay interval $AV_{DDD}$ to AV1 to search for an intrinsic ventricular beat and sets the ventriculoatrial escape interval to CCI−AV1. After a specified number of ventricular senses, the device returns to the primary mode.

As described above, the device may be programmed to switch from the primary mode to the secondary mode if N out of the last K cardiac cycles in the primary pacing mode were ventricular paced cycles, where N and K are specified integers (e.g., 3 and 10, respectively). The device may also be programmed to maintain a count of the number of mode switches from the primary to the secondary pacing mode in an AV response counter, and to continue to operate in the secondary pacing mode with no return to the primary mode if the AV response counter exceeds a specified limit value T. The AV search hysteresis algorithm is also discontinued in the secondary mode if the limit value T is exceeded. This effectively locks the device into the secondary mode until the device is reprogrammed. The device may be further programmed to allow the mode switch history to be reset after a long period of intrinsic AV conduction. Thus, as long as the AV response counter is less than T, the AV response counter is reset upon operating in the primary pacing mode continuously for a specified number S of cardiac cycles (e.g., 1024) without switching to the secondary pacing mode.

It may also be desirable to require a minimum time interval between a ventricular event and an atrial pace. The device may thus be programmed to require that the ventriculoatrial escape interval $VAI_{DDI}$ be greater than or equal to a specified minimum value MinVAI (e.g., 50 ms). When operating in the primary mode, the $AV_{DDI}$ interval may be shortened as necessary in order to enforce the minimum value for $VAI_{DDI}$. If $AV_{DDI}$ is nominally 400 ms and MinVAI is 50 ms, this may be implemented by setting the $AV_{DDI}$ interval as:

$$AV_{DDI}=\min[400 \text{ ms}, CCI-50 \text{ ms}]$$

Alternatively, the sensor-indicated rate may be limited to a maximum value in order to enforce the minimum value for $VAI_{DDI}$ while preserving the $AV_{DDI}$ value which may be implemented by setting the cardiac cycle interval as:

$$CCI=\max[AV_{DDI}+50 \text{ ms}, CCI_{sensor}]$$

where $CCI_{sensor}$ is the sensor-indicated rate.

The device may also be programmed with a safety limit SL (e.g., 2000 ms) which specifies a maximum interval which is allowed to occur between ventricular beats. In order to prevent ventricular pacing at an interval greater than the programmed safety limit SL, the ventriculoatrial interval $VAI_{DDI}$ may be limited to a maximum value such that:

$$VAI_{DDI} \leq SL-AV_{DDI}.$$

Alternatively, the $AV_{DDI}$ interval may be shortened as necessary so that:

$$AV_{DDI} \leq SL-VAI_{DDI}.$$

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for operating an implantable cardiac device with dual-chamber pacing capability in order to provide atrial pacing to a patient in a primary pacing mode and to provide ventricular pacing in a secondary mode upon failure of intrinsic AV conduction, comprising:
   operating the device in a primary DDI pacing mode adjusted to pace only the atria if intrinsic AV conduction is intact; and
   switching the device to a secondary DDD pacing mode if N out of the last K cardiac cycles in the primary pacing mode were ventricular paced cycles, where N and K are specified integers greater than 1.

2. The method of claim 1 wherein the primary and secondary pacing modes are rate-adaptive DDI(R) and DDD(R) modes, respectively.

3. The method of claim 1 wherein:
   (a) the primary pacing mode comprises:
   delivering an atrial pace upon expiration of a ventriculoatrial escape interval $VAI_{DDI}$ unless inhibited by an atrial sense, wherein the $VAI_{DDD}$ interval is triggered by a ventricular event and is derived as:

$$VAI_{DDI}=CCI-AV_S$$

when triggered by a ventricular sense and derived as:

$$VAI_{DDI}=CCI-AV_{DDD}$$

when triggered by a ventricular pace, and where $AV_S$ is a measured intrinsic AV delay interval, $AV_{DDD}$ is the value of a specified atrio-ventricular delay interval, and CCI is a specified cardiac cycle interval representing a desired maximum interval between ventricular beats;
   delivering a ventricular pace upon expiration of a ventricular escape interval VEI unless inhibited by a ventricular sense, wherein the ventricular escape interval is reset by a ventricular pace or a ventricular sense and is set equal to:

$$VEI=CCI+(AV_{DDI}-AV_S)$$

where $AV_{DDI}$ is a desired maximum allowed interval after an atrial pace until a backup ventricular pace is delivered; and,
   (b) the secondary mode comprises:
   delivering a ventricular pace upon expiration of an atrio-ventricular delay interval $AV_{DDD}$ unless inhibited by a ventricular sense, wherein the $AV_{DDD}$ interval is triggered by an atrial pace or sense and is set to a specified value; and,
   delivering an atrial pace upon expiration of a ventriculoatrial escape interval $VAI_{DDD}$ unless inhibited by an atrial sense, wherein the $VAI_{DDD}$ interval is triggered by a ventricular event and is derived as:

$$VAI_{DDD}=CCI-AV_S$$

when triggered by a ventricular sense and derived as:

$$VAI_{DDD}=CCI-AV_{DDD}$$

when triggered by a ventricular pace.

4. The method of claim 3 further comprising operating in the secondary pacing mode for a specified number M of cardiac cycles and then returning to the primary pacing mode.

5. The method of claim 3 further comprising returning to the primary pacing mode from the secondary pacing mode after evidence of intrinsic AV conduction is detected.

6. The method of claim 5 further comprising:
   lengthening the atrio-ventricular delay interval $AV_{DDD}$ for one or more cycles while operating in the secondary pacing mode;
   detecting evidence of intrinsic AV conduction and returning to the primary pacing mode if no ventricular paces are delivered with the lengthened $AV_{DDD}$ interval.

7. The method of claim 6 further comprising:
   modulating the cardiac cycle interval CCI in accordance with a rate-adaptive pacing algorithm so that CCI varies from a base value equal to a specified lower rate limit LRL to a sensor-indicated rate; and,
   wherein the atrio-ventricular delay interval $AV_{DDD}$ is lengthened only if the cardiac cycle interval CCI is not above the lower rate limit LRL by more than a specified limit value.

8. The method of claim 5 further comprising:
   maintaining a count of the number of mode switches from the primary to the secondary pacing mode; and,
   continuing to operate in the secondary pacing mode with no return to the primary mode if the mode switch count exceeds a specified limit value.

9. The method of claim 8 further comprising resetting the count of mode switches upon operating in the primary pacing mode continuously for a specified number S of cardiac cycles without switching to the secondary pacing mode.

10. The method of claim 3 further comprising modulating the cardiac cycle interval CCI in accordance with a rate-adaptive pacing algorithm so that CCI varies from a base value equal to a specified lower rate limit LRL to a sensor-indicated rate.

11. The method of claim 10 further comprising requiring the ventriculoatrial escape interval $VAI_{DDI}$ to be greater than or equal to a specified minimum value MinVAI.

12. The method of claim 11 further comprising shortening the $AV_{DDI}$ interval as necessary in order to enforce the minimum value MinVAI for the ventriculoatrial escape interval $VAI_{DDI}$ when operating in the primary pacing mode.

13. The method of claim 10 further comprising limiting the sensor-indicated rate to a maximum value in order to enforce the minimum value MinVAI for the ventriculoatrial escape interval $VAI_{DDI}$ when operating in the primary pacing mode.

14. The method of claim 3 further comprising preventing ventricular pacing at an interval greater than a programmed safety limit SL by limiting the ventriculoatrial interval $VAI_{DDI}$ to a maximum value such that:

$$VAI_{DDI} \leq SL - AV_{DDI}.$$

15. The method of claim 3 further comprising preventing ventricular pacing at an interval greater than a programmed safety limit SL by shortening the $AV_{DDI}$ interval as necessary so that:

$$AV_{DDI} \leq SL - VAI_{DDI}.$$

16. An implantable cardiac device, comprising:
sensing channels for sensing cardiac activity in an atrium and a ventricle;
pacing channels for delivering paces to an atrium and a ventricle;
a controller for controlling the delivery of paces in accordance with a programmed pacing mode, wherein the controller is programmed to:
operate the device in a primary DDI pacing mode adjusted to pace only the atria if intrinsic AV conduction is intact; and, switch the device to a secondary DDD pacing mode if N out of the last K cardiac cycles in the primary pacing mode were ventricular paced cycles, where N and K are specified integers greater than 1.

17. The device of claim 16 wherein the primary and secondary pacing modes are rate-adaptive DDI(R) and DDD(R) modes, respectively.

18. The device of claim 16 wherein:
(a) the primary pacing mode comprises:
delivering an atrial pace upon expiration of a ventriculoatrial escape interval $VAI_{DDI}$ unless inhibited by an atrial sense, wherein the $VAI_{DDI}$ interval is triggered by a ventricular event and is derived as:

$$VAI_{DDI} = CCI - AV_S$$

when triggered by a ventricular sense and derived as:

$$VAI_{DDI} = CCI - AV_{DDD}$$

when triggered by a ventricular pace, and where AV5 is a measured intrinsic AV delay interval, $AV_{DDD}$ is the value of a specified atrio-ventricular delay interval, and CCI is a specified cardiac cycle interval representing a desired maximum interval between ventricular beats;
delivering a ventricular pace upon expiration of a ventricular escape interval VEI unless inhibited by a ventricular sense, wherein the ventricular escape interval is reset by a ventricular pace or a ventricular sense and is set equal to:

$$VEI = CCI + (AV_{DDI} - AV_S)$$

where $AV_{DDI}$ is a desired maximum allowed interval after an atrial pace until a backup ventricular pace is delivered; and,
(b) the secondary pacing mode comprises:
delivering a ventricular pace upon expiration of an atrio-ventricular delay interval $AV_{DDD}$ unless inhibited by a ventricular sense, wherein the $AV_{DDD}$ interval is triggered by an atrial pace or sense and is set to a specified value; and,
delivering an atrial pace upon expiration of a ventriculoatrial escape interval $VAI_{DDD}$ unless inhibited by an atrial sense, wherein the $VAI_{DDD}$ interval is triggered by a ventricular event and is derived as:

$$VAI_{DDD} = CCI - AV_S$$

when triggered by a ventricular sense and derived as:

$$VAI_{DDD} = CCI - AV_{DDD}$$

when triggered by a ventricular pace.

19. The device of claim 18 wherein the controller is further programmed to operate in the secondary pacing mode for a specified number M of cardiac cycles and then returning to the primary pacing mode.

20. The device of claim 18 wherein the controller is further programmed to return to the primary pacing mode from the secondary pacing mode after evidence of intrinsic AV conduction is detected.

* * * * *

UNITED STATES PATENT AND TRADEMARK OFFICE
CERTIFICATE OF CORRECTION

| | | |
|---|---|---|
| PATENT NO. | : 7,257,442 B2 | Page 1 of 1 |
| APPLICATION NO. | : 10/854736 | |
| DATED | : August 14, 2007 | |
| INVENTOR(S) | : Kramer et al. | |

It is certified that error appears in the above-identified patent and that said Letters Patent is hereby corrected as shown below:

In column 7, Line 46, in Claim 1, delete "and" and insert -- and, --, therefor.

In column 10, Line 7 (Approx.), in Claim 18, delete "AV5" and insert -- $AV_s$ --, therefor.

Signed and Sealed this

Twentieth Day of November, 2007

JON W. DUDAS
*Director of the United States Patent and Trademark Office*